United States Patent
Lin et al.

(12) 
(10) Patent No.: US 7,029,675 B1
(45) Date of Patent: Apr. 18, 2006

(54) HEPSIN ANTAGONIST AND METHODS OF USE

(76) Inventors: Shu-Wha Lin, No. 3, 3rd floor, Lane 6, Fu-Te North Road, San-Chung, Taipei (TW) 241; I-Shing Yu, 5 Fl., No. 6, Lane 52, Sec. 3, Huanhe Z. Rd., Yunghe City, Taipei County, Taipei (TW) 234; Teng-Nan Lin, Rm 404 IBMS, Academia Sinica, Taipei 11529 (TW) 11529; Pao-Hsien Chu, 5216 Quaker Hill La., San Diego, CA (US) 92130; Hosheng Tu, 15 Riez, Newport Beach, CA (US) 92657

( * ) Notice: Subject to any disclaimer, the term of this patent is extended or adjusted under 35 U.S.C. 154(b) by 240 days.

(21) Appl. No.: 10/454,146

(22) Filed: Jun. 4, 2003

(51) Int. Cl.
*A61K 39/395* (2006.01)

(52) U.S. Cl. ............................... 424/133.1; 424/146.1; 435/6

(58) Field of Classification Search ............. 424/133.1, 424/146.1; 435/6
See application file for complete search history.

(56) References Cited

U.S. PATENT DOCUMENTS

| 5,981,830 | A | 11/1999 | Wu et al. |
| 6,423,543 | B1 | 7/2002 | Marcotte et al. |
| 6,563,015 | B1 | 5/2003 | Stern et al. |

FOREIGN PATENT DOCUMENTS

| WO | WO 97/47651 | * 12/1997 |

OTHER PUBLICATIONS

Rutsch et al. Herz, Dec. 1994: 19(6): 336-352, German Document, Abstract only.*
Torres-Rosado A., et al., "Hepsin, a Putative Cell-Surface Serine Protease, is Required for Mammalian Cell Growth" Proc. Natl. Acad. Sci. USA vol. 90, pp. 7181-7185, Aug. 1993.
Kazama Y. et al., "Hepsin, a Putative Membrane-Associated Serine Protease, Activates Human Factor VI and Initiates a Pathway of Blood Coagulation on the Cell Surface Leading to Thrombin Formation" The Journal of Biological Chemistry, vol. 270, No. 1, pp. 66-72, 1995.
Zacharski L.P. et al, "Expression of the Factor VII Activating Protease, Hepsin, In Situ in Renal Cell Carcinoma" Thromb Haemost 1998; 79: 876-877.
Dissmann R. et al., "Estimation of Enzymatic Infarct Size: Direct Comparison of the Marker Enzymes Creatine Kinase and -Hydroxybutyrate Dehydrogenase" Am Heart J 135(1): 1-9, 1998.
Product Brochure "100022 Hepsin Polyclonal Antibody Affinity-Purified (AA 241-260)" Cayman Chemical Company 2003.
Product Brochure "100024 Hepsin Blocking Peptide (AA 241-260)" Cayman Chemical Company 2003.

* cited by examiner

*Primary Examiner*—Patrick J. Nolan
*Assistant Examiner*—Yunsoo Kim

(57) ABSTRACT

A method for treating or preventing infarction of a patient comprising administering a hepsin antagonist with a dosage effective to suppress or inactivate hepsin's expression over a sustained period.

8 Claims, 4 Drawing Sheets

Hepsin KO Mice

Wild Mice

HEPSIN ANTAGONIST AND METHODS OF USE

FIELD OF THE INVENTION

The present invention generally relates to a new class of antagonists to inactivate functions of serine protease, especially hepsin. More particularly, the present invention relates to hepsin antagonists, inhibitors or anti-hepsin antibodies that effectively reduce infarction volume by inactivating or suppressing the gene's expression.

BACKGROUND OF THE INVENTION

Hepsin is a novel serine protease of the trypsin family and contains a transmembrane domain near its amino-terminus. The structural feature distinguishes hepsin from most other serine proteases. Biochemical studies indicate that hepsin is a type II transmembrane serine protease expressed mainly on the surface of hepatocytes. Hepsin has an extra-cellular proteolytic domain and exhibits low sequence homology to other known proteases. Lower levels of hepsin mRNA are detected in other tissues including lung, kidney, pancreas, stomach, thyroid and prostate. In addition, hepsin mRNA is present in several human tumor cell lines, such as hepatoma cells HepG2 and PLC/PRF/5, mammary cancer cells MCF784 and T470, and epitheloid carcinoma cells HeLa S3 (Torres-Rosado, A. et al., Proc. Natl. Acad. Sci. USA 1993; 90:7181–7185). Further in vitro studies have shown inhibition of hepatoma cell proliferation using hepsin inhibitors (Torres-Rosado, A. et al. Proc. Natl. Acad. Sci. USA 1993; 90:7181–7185). Recently, hepsin overexpression was observed in prostate, breast, kidney and ovarian cancers and due to low homology to other known proteases, it may provide a unique target for pharmacological or interventional therapy.

U.S. Pat. No. 5,981,830 issued on Nov. 9, 1999, entire contents of which are incorporated herein by reference, discloses nucleotide and amino acid hepsin sequence. The U.S. Pat. No. 5,981,830 patent further discloses a transgenic mouse comprising a disrupted hepsin gene and methods of making the transgenic mouse comprising the disrupted hepsin gene by utilizing a hepsin targeting vector for homologous recombination in mouse embryonic stem cells.

Hepsin is necessary for cell growth in vitro and may play a role in metastatic expansion by factor VII (a blood coagulation factor) activation, thereby initiating a coagulation pathway on the cell surface that leads to thrombin formation (Kazama et al., J. Biol. Chem. 1995;270:66–72). The observed molecular mass of hepsin by immunoblotting is 45.3 kDa. Cloning and characterization of the mouse and rat hepsin indicate 88% overall homology with human hepsin.

More recently, a connection between the role of hepsin in coagulation and the neoplastic phenotype was suggested. It was demonstrated that hepsin is highly expressed in renal cell carcinoma, and from these results it was proposed that hepsin might be the initiator of tumor cell-induced thrombin generation in certain tumors that lack tissue factor expression (Zacharski et al., Thromb. Haemost., 1998;79:876–877).

Several in vitro studies have suggested that hepsin may play a role in blood coagulation, hepatocyte growth, and fertilization. To determine the functional importance of hepsin, hepsin-deficient mice were generated by homologous recombination. Homozygous hepsin-deficient mice were viable and fertile, and grew normally. When analyzed in hemostasis assays, such as tail bleeding time and plasma clotting times, and in vivo modes, such as disseminated intravascular coagulation, septic shock, and acute liver regeneration, hepsin-deficient mice had similar phenotypes as wild-type controls. Liver weight and serum concentrations of liver-derived proteins or enzymes were also similar in hepsin-deficient and wild-type mice. No abnormalities were identified in major organs in hepsin-deficient mice in histological examinations. These results indicate that hepsin is not an essential enzyme for normal hemostasis, embryogenesis, and maintenance of normal liver function. Unexpectedly, serum concentrations of bone-derived alkaline phosphatase were approximately two-fold higher in both male and female hepsin-deficient mice than those in wild-type controls. The underlying mechanism for this phenotype and long-term effects of hepsin deficiency remain to be determined.

Hepsin might be involved in the development of prostate cancer. If a target drug were to be developed to inhibit hepsin, it appears that this drug would have the potential to be effective for a majority of prostate cancer patients. And since hepsin appears to be excessively produced in most prostate cancers, chemicals that block the actions of hepsin could possibly prevent prostate cancer from developing or progressing. It is one aspect of the present invention to provide a method for treating prostate cancer of a patient comprising administering a hepsin antagonist with a dosage effective to suppress or inactivate hepsin's expression, particularly site specifically at the target tissue by local administration. A dosage of hepsin antagonist herein may consist one dose or multiple doses administered over time.

Prostate cancer is the most commonly diagnosed noncutaneous cancer in men. Despite this fact, many of the genetic changes that coincide with prostate cancer progression remain enigmatic. The expression profiles of several benign and malignant human prostate samples have been characterized and identified with several genes that are differentially expressed between benign and malignant glands. One gene that was overexpressed encodes the serine protease hepsin. In situ hybridization demonstrates that hepsin is specifically overexpressed in the carcinoma cells themselves. These facts, together with the molecular properties of hepsin, make it an ideal target for prostate cancer therapy (Magee J A, et al. Cancer Research 2001;61(15):5692–5696)

SUMMARY OF THE INVENTION

In general, it is one object of the present invention to provide a method for treating infarction of a patient comprising administering a hepsin antagonist with a dosage effective to suppress or inactivate hepsin's expression. A dosage of hepsin antagonist herein may consist one dose or multiple doses administered over time. In one embodiment, the infarction is cerebral infarction or myocardial infarction.

It is another object of the present invention to provide a method for treating infarction of a patient with the hepsin antagonist selected from a group consisting of anti-hepsin antibodies, hepsin blockers, dominant mutant protein/peptide antagonists, dominant mutant receptor antagonists, hepsin-specific antisense oligonucleotides, hepsin-specific serine protease inhibitors, hepsin-specific siRNA, and combination thereof. In one preferred embodiment, the step of administering the hepsin antagonist comprises delivering the hepsin antagonist orally. In another embodiment, the step of administering the hepsin antagonist comprises delivering the hepsin antagonist through an apparatus to the infarcted site or a site adjacent to the infarction, wherein the apparatus is a probe, a catheter or a cannula.

In some aspects, the step of administering the hepsin antagonist for treating infarction is carried out pre-infarctedly when the symptom of infarction appears. In one preferred embodiment, the step of administering the hepsin antagonist for treating infarction is carried out within about 12 hours post-infarctedly. In another embodiment, the step of administering the hepsin antagonist is preferably carried out within about 30 minutes post-infarctedly.

It is a further object of the present invention to provide a method for treating infarction of a patient comprising administering a hepsin antagonist to an infarcted region or an infarct-risk region that is adjacent to the infarcted region effective to suppress or inactivate hepsin's expression at about the infarcted/infarct-risk region.

In some aspects, it is provided a method for preventing infarction of a patient comprising administering a hepsin antagonist effective to suppress or inactivate hepsin's expression for preventing infarction, wherein the hepsin antagonist is selected from a group consisting of anti-hepsin antibodies, hepsin blockers, dominant mutant protein/peptide antagonists, dominant mutant receptor antagonists, hepsin-specific antisense oligonucleotides, hepsin-specific siRNA, hepsin-specific serine protease inhibitors, and combination thereof.

In a further embodiment, the step of administering the hepsin antagonist is selected from a group consisting of oral administration, intramuscular injection, transdermal injection, intravenous injection, or inhalation, wherein the hepsin antagonist may comprise a pharmaceutically acceptable carrier or diluent.

BRIEF DESCRIPTION OF THE DRAWINGS

Certain preferred embodiments and modifications thereof will become apparent to those skilled in the art from the detailed description herein having reference to the figures that follow, of which.

DETAILED DESCRIPTION OF EXEMPLARY EMBODIMENTS

Figure 1:
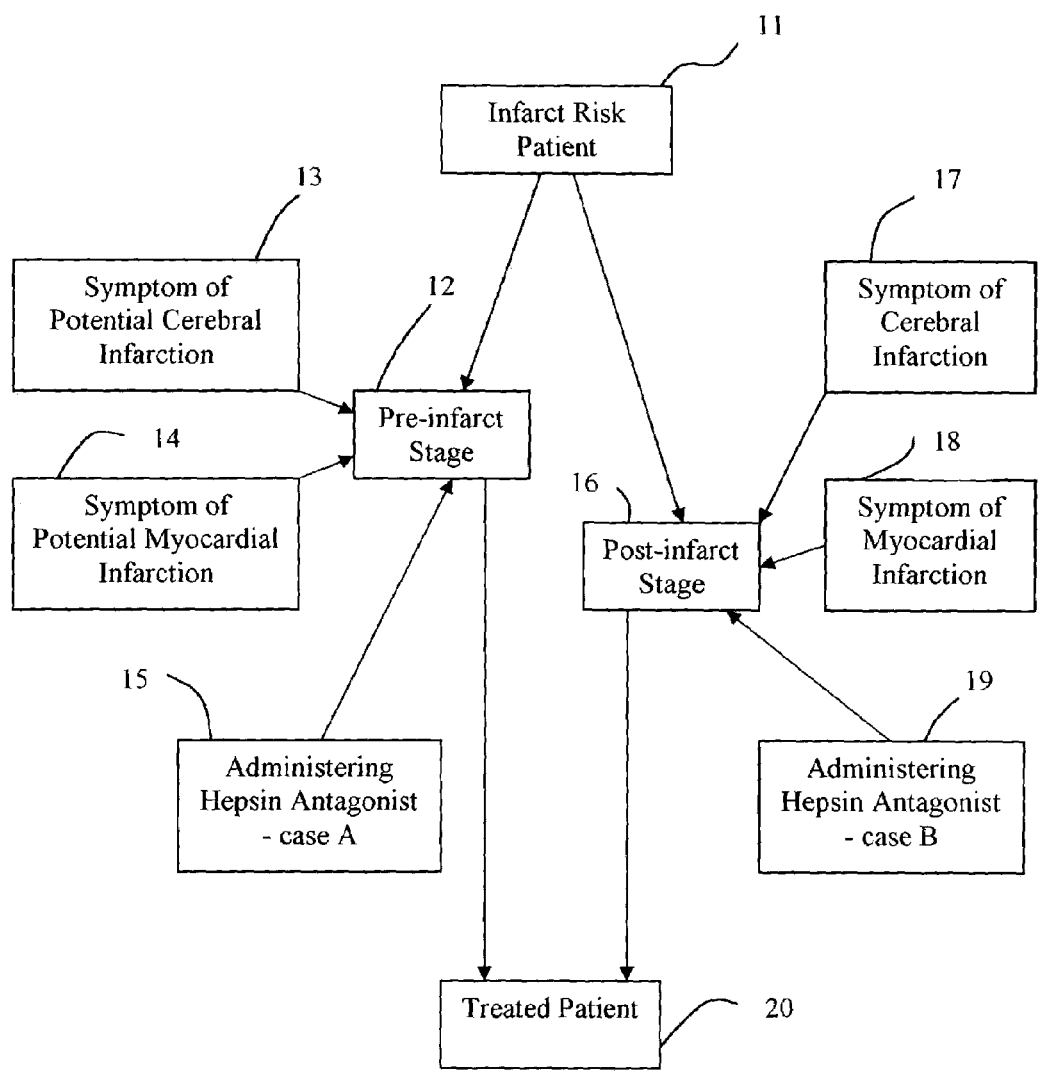
FIG. 1 shows a schematic diagram of treating infarction of a patient.

The following detailed description is of the best presently contemplated modes of carrying out the invention. This description is not to be taken in a limiting sense, but is made merely for the purpose of illustrating general principles of embodiments of the invention.

Hepsin is a type II membrane-associated protein that has an extra-cellular proteolytic domain and exhibits low sequence homology to other known proteases. U.S. Pat. No. 5,981,830 issued on Nov. 9, 1999, entire contents of which are incorporated herein by reference, discloses nucleotide and amino acid hepsin sequence. The term "hepsin" is herein intended to include the nucleotide and amino acid sequence as outlined in the U.S. Pat. No. 5,981,830. The term "hepsin antagonist" is herein intended to mean any substance, factor or agent in any formula, form or quantity that has the property or activity to inactivate or suppress the hepsin gene's expression. The hepsin antagonist may be selected from a group consisting of anti-hepsin antibodies, hepsin blockers, dominant mutant protein/peptide antagonists, dominant mutant receptor antagonists, hepsin-specific antisense oligonucleotides, hepsin-specific siRNA, hepsin-specific serine protease inhibitors, combination thereof, and the like.

Hepsin was previously identified as a putative cell-surface serine protease. When hepatoma cells were treated with anti-hepsin antibodies (for example, HAbP5), their growth was substantially arrested, suggesting the requirement of hepsin molecules present at the cell surface for normal cell growth. This was further supported by a gross inhibition of cell growth with hepsin-specific antisense oligonucleotides. Upon treatment of cells with antisense oligonucleotides, rapid reduction in cellular hepsin was observed. This reduction in cellular hepsin levels was accompanied by drastic morphological changes. Various tissues in the developing mouse embryo showed greatly elevated hepsin levels in regions of active proliferation. These results indicate that hepsin plays an essential role in cell growth and maintenance of cell morphology (Torres-Rosado, A. et al., Proc. Natl. Acad. Sci. USA 1993;90:7181–7185).

Extracellular proteases mediate the digestion of neighboring extracellular matrix components in initial tumor growth, allow shedding or desquamation of tumor cells into the surrounding environment, provide the basis for invasion of basement membranes in target metastatic organs, and are required for release and activation of many growth and angiogenic factors. In one example, experimental evidence indicates that hepsin, a cell surface serine protease identified in hepatoma cells, is overexpressed in ovarian cancer. Hepsin is a serine protease found in most tissues, abundant in the liver. It is a membrane associated protein and is not found in the cytosol. Hepsin does not appear to be essential for development or homeostasis. On Northern blot analysis, the hepsin transcript was abundant in carcinoma but was almost never expressed in normal adult tissue, including normal ovary, suggesting that hepsin is frequently overexpressed in ovarian tumors and therefore may be a candidate protease in the invasive process and growth capacity of ovarian tumor cells. For more information, see: Tanimoto H, et al., Cancer Res. 1997;57(14):2884–2887; Leytus, et al., Biochemistry 1988;27:1067–1074; Tsuji A, et al., J. Biol. Chem. 1991; 266:16948–16953; and Wu, Q., et al., J. Clin. Invest. 1998; 101:321–326.

Protease proteins, particularly members of the hepsin subfamily, are a major target for drug action and development. Accordingly, it is valuable to the field of pharmaceutical development to identify and characterize previously unknown members of this subfamily of protease proteins. The present invention advances the state of the art by providing a method of treating or preventing infarction by administering a hepsin antagonist with a dosage effective to suppress or inactivate hepsin's expression. A dosage of hepsin antagonist herein may consist one dose or multiple doses administered over time, wherein each dose may contain hepsin antagonist with varying concentration, amount or composition.

Functional inactivation refers to a partial or complete reduction of the expression of at least a portion of a polypeptide encoded by an endogenous serine protease gene of a single cell, selected cells or all of the cells of a mammal. In accordance with the present invention, a serine protease gene (for example, hepsin) is inactivated in such a manner that is effective to reduce expression of the corresponding gene product. Thus, e.g., a functionally reduced recombinant hepsin gene does not express a functional hepsin polypeptide or expresses a functional hepsin polypeptide at levels that are less than the levels found in normal, e.g., reduced by 70%, 80%, 85%, 90%, 95%, 99%, or more. The gene may be modified or inactivated in any of the effective positions, e.g., enhancers, promoters, regulatory regions, noncoding sequences, coding sequences, introns, exons, etc., so as to decrease or prevent expression of that gene in the cell.

In some aspects, molecular analysis of human tumors provides hope for earlier cancer detection as well as for subtyping of cancers into those with different prognosis or alternative treatment modalities. DNA microarrays enable one to measure relative levels of mRNAs of thousands of genes simultaneously from any given sample. mRNA expression profiling of large subsets of genes by microarray-based studies has already been successfully employed to subclassify diffuse, large B-cell lymphomas and acute leukemias. The identification of a small set of genes whose expression levels could be used as markers for cancer diagnosis and outcome prediction is crucial to the translation of data from microarrays into routine clinical use. One of the ways is by evaluating the most promising markers individually to assess their clinical relevance.

A recent study by Chinnaiyan (Nature Oct. 10, 2002) investigated prostate cancers using a microarray containing almost 10,000 human cDNAs. They examined the gene expression profiles of over 50 normal or cancerous prostate tissue specimens in addition to three cell lines derived from metastatic prostate cancer. Clustering of tumors according to their gene expression profiles was found to correspond to the four different clinical states of the prostate specimens. Normal prostate tissue and benign conditions such as benign prostatic hyperplasia formed a cluster that was distinct from all malignant conditions. Moreover, localized forms of prostate cancer could be easily distinguished from metastatic prostate cancer based on patterns of gene expression. Some aspects of the invention relates to a method for preventing cancer and/or tumor of a patient comprising administering a hepsin antagonist effective to suppress or inactivate hepsin's expression for preventing cancer and/or tumor. Further, some aspects of the invention relates to a method for treating cancer and/or tumor of a patient comprising administering a hepsin antagonist effective to suppress or inactivate hepsin's expression for treating cancer and/or tumor.

The serum level of prostate-specific antigen (PSA) is traditionally used in the diagnosis and monitoring of prostate cancer. However, the use of PSA serum levels is complicated by the fact that it may also be elevated in certain benign conditions of the prostate. Dhanasekaran et al. (Nature 2001;412:822–826) chose two genes, hepsin, encoding a transmembrane serine protease and PIM-1, encoding a serine threonine kinase, that were upregulated in prostate cancer for further evaluation by immunohistochemistry. Tissue microarrays on glass slides containing 738 prostate samples were used for staining with anti-hepsin antibody or 810 prostate samples with anti-PIM1 antibody. It was found that in addition to localized and metastatic prostate cancer, an early lesion of prostate cancer termed HG-PIN, showed an increased expression of hepsin protein. PIM1, on the other hand, was expressed at moderate to high levels in almost half of prostate cancer specimens and was absent or weak in HG-PIN or normal prostate tissue. Since the investigators had access to follow up clinical data on a majority of the patients, an outcome analysis was performed that showed a correlation between decreased expression of hepsin and PIM1 proteins with poor patient outcome. Recently, hepsin overexpression was observed in prostate, breast, kidney and ovarian cancers and due to low homology to other known proteases, it may provide a unique target for pharmacological or interventional therapy. Some aspects of the invention relates to a method for treating or preventing cancer of a patient comprising administering a hepsin antagonist effective to suppress or inactivate hepsin's expression for treating or preventing cancer, wherein the cancer is selected from a group consisting of prostate cancers, breast cancers, kidney cancers, ovarian cancers and other cancers.

The identification of potential targets is cumbersome due to patients as well as experimental variability in addition to the complexity of molecular alterations in cancer. Discovery of novel cancer markers that are correlated with patient outcome requires considerable effort. One obvious approach is to delineate a number of markers by microarray analysis followed by validation of a chosen set in patient samples such as tissue microarrays as performed in this study. This is especially important as the level of mRNA may not correlate too well with protein levels. Alternative proteomic methods based on two-dimensional gel electrophoresis or mass spectrometry are more difficult due to larger amounts of protein required for identification which may not be available for tumors such as the prostate cancer. The results are bound to stimulate adoption of an integrated approach to the discovery of not only cancer related but also other disease-specific biomarkers or markers.

The identification of new serine proteinases and kinases permits the development of a range of derivatives, agonists and antagonists at the nucleic acid and protein levels which in turn have applications in the treatment and diagnosis of a range of conditions such as cancer, inflammation, neurological disorders amongst many other conditions including conditions which initiate or promote apoptosis such as viral infection, old age and drug abuse.

FIG. 1 shows a schematic diagram of treating infarction. Some aspects of the present invention provides a method for treating infarction of a patient comprising administering a hepsin antagonist at a dosage effective to suppress or inactivate hepsin's expression. The administration may comprise a plurality of doses of hepsin antagonist, wherein each doses is the same quantity or varying quantity/concentration according to the need. In one embodiment, the dosage may comprise hepsin antagonist with a pharmaceutically acceptable carrier or diluent. In another embodiment, the dosage comprises hepsin antagonist compounded with a carrier adapted for slow release of the hepsin antagonist over time. An infarcted risk patient 11 may encounter a pre-infarct stage 12 by feeling some symptoms of potential cerebral infarction 13 or symptoms of potential myocardial infarction 14, such as dizziness, shortness of breath, ischemia or the like. The symptoms may also come from examination or diagnosis, such as elevation of a biological marker in the body fluid. Once the infarct risk patient 11 feels at risk of infarction, hepsin antagonist for case A 15 may be administered.

This administration of hepsin antagonist may be as early as 12 hours before the infarction, though it is difficult to pre-time the occurrence of infarction. Preferably, the administration of hepsin antagonist is within about 30 minutes before the infarction. Any conventional methods may be used to administer the hepsin antagonist, such as oral administration (in liquid suspensions or tablets), intramuscular injection with a needle, intravenous injection with a needle, transdermal injection with a needle, or inhalation through the throat or nose. Other method for administering the hepsin antagonist may be through an apparatus to the infarcted site or infarct-risk site, wherein the apparatus is a probe, a catheter or a cannula. The fabrication and operations of a probe, a catheter or a cannula are well known to one skilled in the art. The "infarct-risk site" is herein intended to mean the site adjacent to an infarcted region that is vulnerable or risk to infarct unless appropriate means for preventing future infarction is taken promptly.

Some aspects of the present invention relates to a method for treating infarction of a patient comprising administering a hepsin antagonist to an infarcted region or infarct-risk region with a dosage effective to suppress or inactivate hepsin's expression at about the infarcted/infarct-risk region. A dosage of hepsin antagonist herein may consist one dose or multiple doses administered over time. An infarcted risk patient 11 may encounter a post-infarct stage 16 by encountering some symptoms of cerebral infarction 17 or symptoms of myocardial infarction 18. Once the infarct risk patient 11 encounters infarction, hepsin antagonist for case B 19 may be administered. This administration of hepsin antagonist may be as late as 12 hours or later after the infarction. Preferably, the administration of hepsin antagonist is about within 30 minutes to 90 minutes after the infarction. Any conventional methods may be used to administer the hepsin antagonist, such as oral administration, intramuscular injection with a needle, intravenous injection with a needle, transdermal injection with a needle, inhalation, or delivering the hepsin antagonist through an apparatus to the infarcted or infarct-risk site, wherein the apparatus is a probe, a catheter or a cannula. The treated patient 20 with the hepsin antagonist administered pre-infarctedly or post-infarctedly shall result in a minimal infarct volume.

Other than oral administration, hepsin antagonist can be delivered to the local infarcted area by percutaneous delivery with a catheter, a probe or a cannula as described above. In one preferred embodiment, the apparatus comprises a tip and a tip section where the hepsin antagonist is to be delivered into the infarcted or infarct-risk area by inserting the tip into the target tissue. In some embodiment, the hepsin antagonist is continually supplied through a lumen of the apparatus from an outside source. In another embodiment, the hepsin antagonist is administered from the reservoir located at about the tip section. In still another embodiment, the hepsin antagonist is loaded with an implant that is to stay behind when the apparatus is removed from the body. The implant may contain the hepsin antagonist formulated and configured for slow release over a desired period of time.

Figure 2:
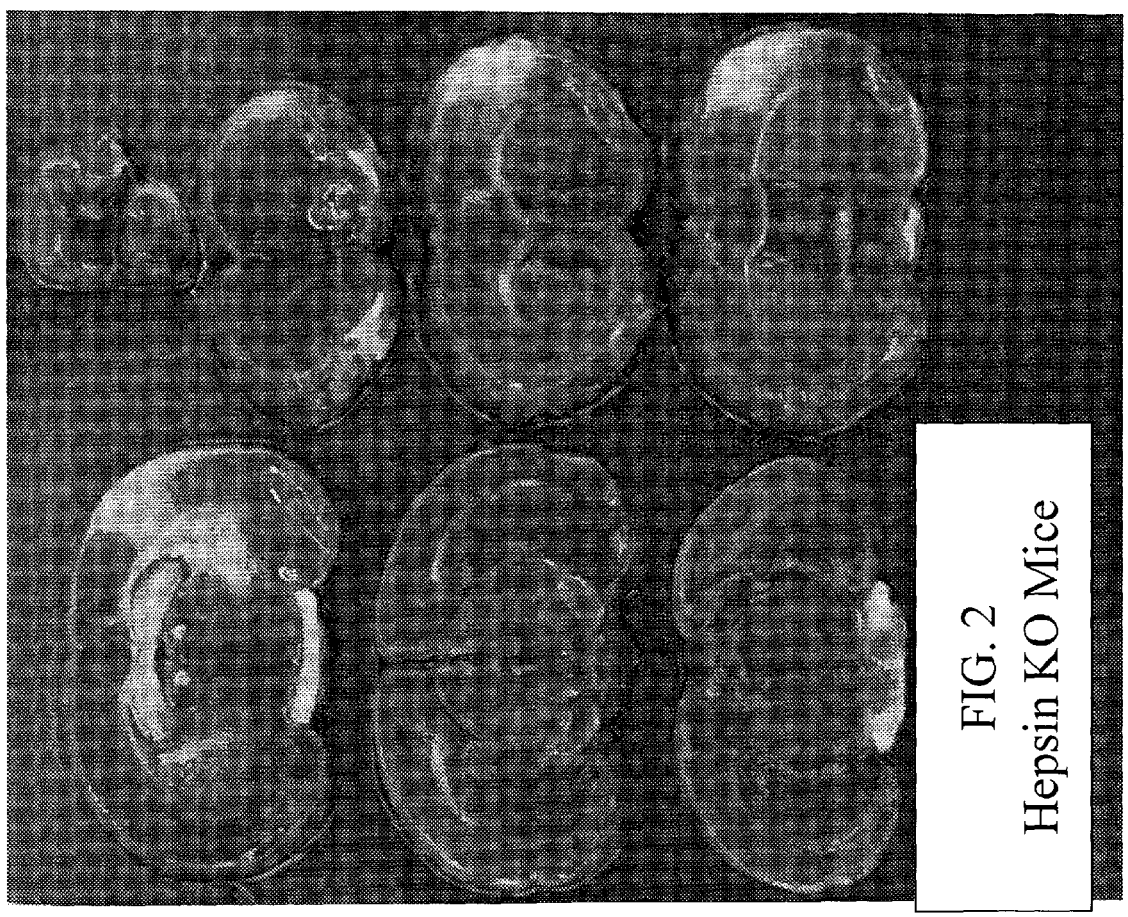
FIG. 2 shows the infarcted cerebral tissue in hepsin-deficient mice.
Figure 3:
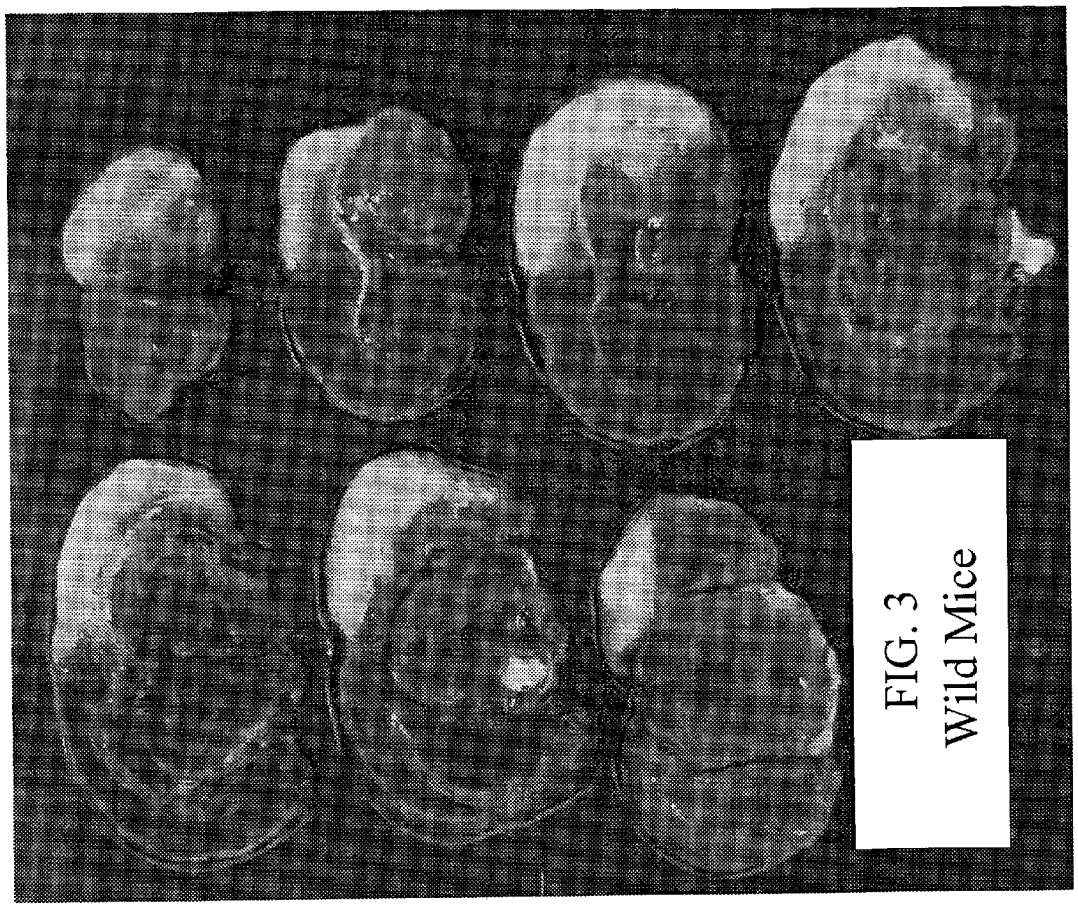
FIG. 3 shows the infarcted cerebral tissue in wild-type mice.

FIG. 2 shows the infarcted cerebral tissue in hepsin-deficient mice, while FIG. 3 shows the infarcted cerebral tissue in wild-type mice. The hepsin-deficient mice and wild-type mice are selected for cerebral infarction studies. The general procedures for providing hepsin-deficient mice and wild-type mice follow the methods as described in the article by Wu (J. Clin. Invest. 1998;101:321–326) and/or in U.S. Pat. No. 5,981,830, entire contents of both are incorporated herein by reference. The blood flow to the carotid system is temporarily blocked for a constant time in each mouse, and the animals are sacrificed for visual observation and measurement. The white area or volume relates to the infarction while the transitional zone between the red and white zones may be related to the infarct-risk region that could be treated acutely as taught in the invention.

Occlusion of an artery produces an area of coagulative necrosis downstream. This area of coagulative necrosis is known as an infarct. The infarct may comprise cerebral infarct, myocardial infarct, splenic infarct, hemorrhagic infarct of small intestine, multi-infarct dementia, renal infarct of the kidney, infarct in the liver, spinal cord infarct, infarct of the inferior wall, and the like. Splenic infarct is a rare form of pathology. The infarct may be segmental or global, involving the entire organ. It is the result of arterial or venous compromise, and it is associated with a heterogeneous group of diseases. Surgery is indicated only in the presence of complications such as hemorrhage, rupture, abscess, or pseudocyst. Some aspects of the invention relates to a method for treating infarction of a patient comprising administering a hepsin antagonist with a dosage effective to suppress or inactivate hepsin's expression from cerebral, myocardial or splenic infarction.

Figure 4:
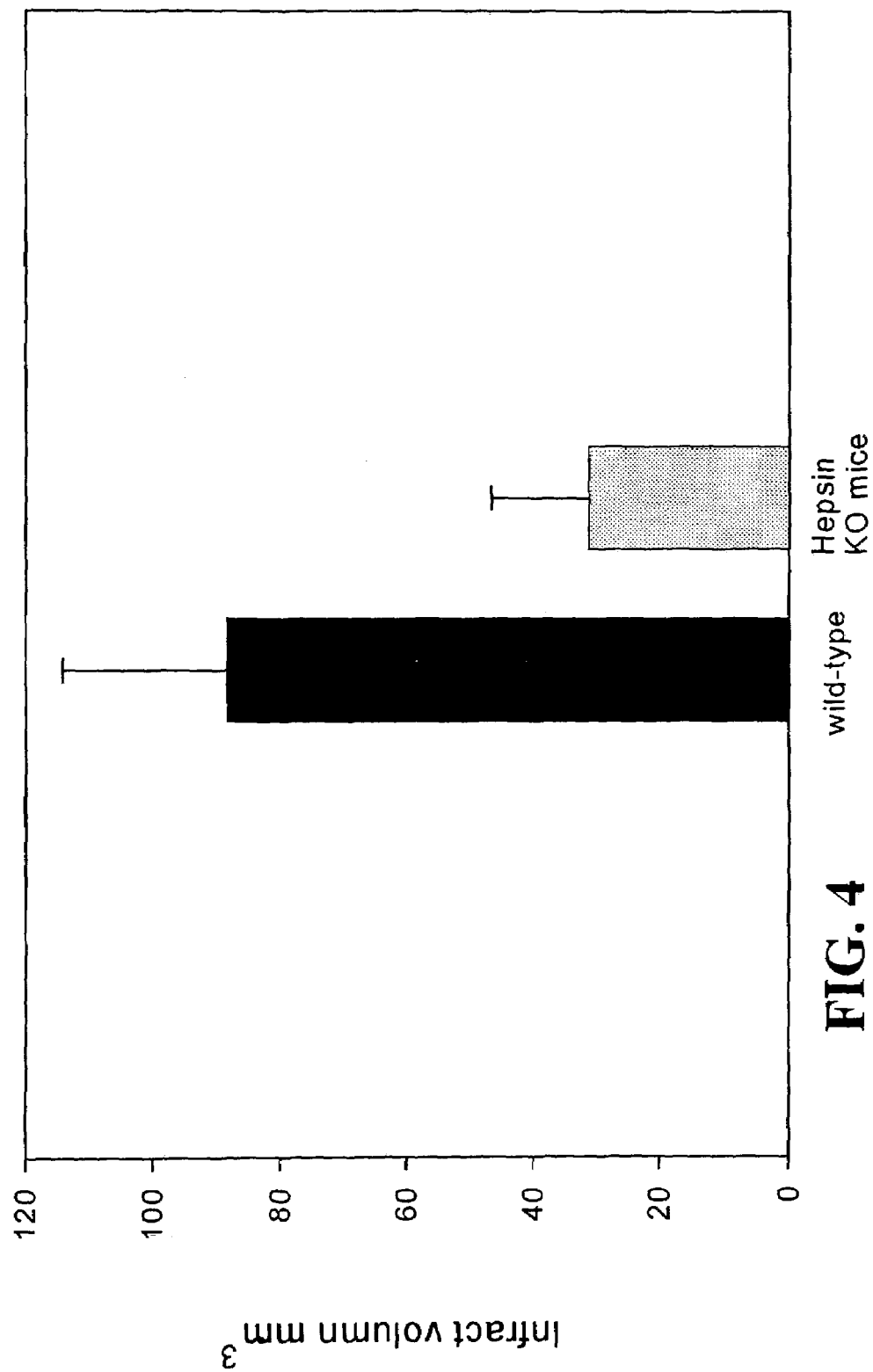
FIG. 4 shows the infarct volume comparison between hepsin-deficient mice and wild-type mice.

FIG. 4 shows the infarct volume comparison between the hepsin-deficient mice and wild-type mice from the above-disclosed study. The average infarcted cerebral volume for hepsin-deficient mice is about 31 $mm^3$ while the average infarcted cerebral volume for wild-type mice is about 80 $mm^3$. The study shows more than 60% reduction of infarct volume with the hepsin-deficient mice as compared to wild-type mice, suggesting a method for preventing for preventing myocardial infarction or cerebral infarction of a patient comprising administering a hepsin antagonist effective to suppress or inactivate hepsin's expression. In one embodiment, the hepsin antagonist is selected from a group consisting of anti-hepsin antibodies, hepsin blockers, dominant mutant protein/peptide antagonists, dominant mutant receptor antagonists, hepsin-specific antisense oligonucleotides, hepsin-specific siRNA, hepsin-specific serine protease inhibitors, and combination thereof.

Estimation of infarct size with serum-time activity curves of creatine kinase (CK) (or CKMB) or -hydroxybutyrate dehydrogenase (HBDH) is widely used in clinical trials. However, an independent variable such as left ventricular function has not been directly compared with CK and HBDH infarct size measurements in the same group of patients. For comparative clinical trials HBDH appears to be the preferable marker enzyme for estimates of infarct size and measure of reperfusion effectiveness. In clinical practice one routine measure of HBDH serum activity on the second day after infarction may be a useful approximate value of infarct size. (Dissmann R et al., Am Heart J. 1998;135(1): 1–9)

siRNA means herein "short or small interfering RNA" that may comprise double-stranded unmodified RNA. RNA interference, or siRNA, is a phenomenon in which double stranded RNA effects silencing of the expression of genes that are highly homologous to either strand of the RNA in the duplex. Gene silencing in siRNA results from the degradation of mRNA sequences, and the effect has been used to determine the function of many genes in *Drosophilia, C. elegans*, and many plant species. The duration of knockdown by siRNA can typically last for 7–10 days, and has been shown to transfer to daughter cells. Of further note, siRNAs are effective at quantities much lower than alternative gene silencing methodologies, including antisense and ribozyme based strategies (Elbashir S M et al., Nature 2001;422:494–498). Using siRNA for gene slicing is a rapidly evolving tool in molecular biology.

Due to various mechanisms of antiviral response to long double-strand RNA, siRNA at first proved more difficult to establish in mammalian species. Certain study discovered that siRNA can be elicited very effectively by well-defined 21-base duplex RNAs (Elbashir S M et al, Genes and Dev. 2001;15:188–200). When these small interfering RNA, or siRNA, are added in duplex form with a transfection agent to mammalian cell cultures, the 21-base-pair RNA acts in concert with cellular components to silence the gene with sequence homology to one of the siRNA sequences. Strategies for the design of effective siRNA sequences have been recently documented. The studies of mammalian siRNA suggest that the most efficient gene-silencing effect is achieved using double-stranded siRNA having a 19-nucleotide complementary region and a 2-nucleotide 3' overhang at each end. Current models of the siRNA mechanism suggest that the antisense siRNA strand recognizes the specific gene target. In gene-specific siRNA, the coding region (CDS) of the mRNA is usually targeted.

One of the most rapidly growing applications utilizing RNA oligonucleotides is gene silencing with siRNA. The phenomenon of gene silencing with siRNA was first observed in 1996 and in 2001 the underlying mechanisms and steps in the cell's metabolism were understood in more detail (Nykanen A. et al., Cell 2001;107:309–321). Like knockout-strains of model organisms and antisense applications this technology is a very powerful and straight forward way to assess the effect of shutting down the expression of specific genes, for example, hepsin. The mechanism and efficiency of siRNA technology allows to overcome many of the limitations and obstacles of the techniques. Therefore this siRNA technique helps to effectively establish an understanding of gene functions. Also the therapeutic use in some diseases like cancer or a variety of viral infections is a promising option.

Antagonists of proteinase/kinase expression include antisense molecules, ribozymes and co-suppression molecules. Agonists include molecules which increase promoter ability or interfere with negative regulatory mechanisms. Agonists of proteinase/kinase include molecules which overcome any negative regulatory mechanics. Antagonists of the proteinase/kinase include antibodies and inhibitor peptide fragments.

U.S. Pat. No. 6,423,543 issued on Jul. 23, 2002, entire contents of which are incorporated herein by reference, discloses antisense compounds, compositions and methods that are provided for modulating the expression of hepsin. The compositions comprise antisense compounds, particularly antisense oligonucleotides, targeted to nucleic acids encoding hepsin. Methods of using these compounds for modulation of hepsin expression and for treatment of diseases associated with expression of hepsin are disclosed in the above-incorporated U.S. Pat. No. 6,423,543.

In the method for treating or preventing infarction of a patient, the step of administering the hepsin antagonist is selected from a group consisting of oral administration, intramuscular injection, transdermal injection, intravenous injection, or inhalation.

In a further embodiment, the hepsin antagonist for oral administration may be compounded with a carrier adapted for slow release of the hepsin antagonist. In a preferred embodiment, the hepsin antagonist comprises a pharmaceutically acceptable carrier or diluent. Other suitable formulation with the hepsin antagonist in any conventional package is also included within the scope of the invention.

The invention provides pharmaceutical compositions that can be administered to a patient to achieve a therapeutic effect. Pharmaceutical compositions of the invention can comprise a hepsin antagonist for a transmembrane serine protease polypeptide, transmembrane serine protease polynucleotide, antibodies which specifically bind to a transmembrane serine protease polypeptide, or inhibitors of a transmembrane serine protease polypeptide. The compositions can be administered alone or in combination with at least one other agent, such as stabilizing compound, which can be administered in any sterile, biocompatible pharmaceutical carrier, including, but not limited to, saline, buffered saline, dextrose, and water. The compositions can be administered to a patient alone, or in combination with other agents, drugs or hormones.

In addition to the active ingredients, these pharmaceutical compositions can contain suitable pharmaceutically-acceptable carriers comprising excipients and auxiliaries that facilitate processing of the active compounds into preparations which can be used pharmaceutically. Pharmaceutical compositions of the invention can be administered by any number of routes including, but not limited to, oral, intravenous, intramuscular, intra-arterial, intramedullary, intrathecal, intraventricular, transdermal, subcutaneous, intraperitoneal, intranasal, parenteral, topical, sublingual, or rectal means. Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents can be added, such as the cross-linked polyvinyl pyrrolidone, agar, alginic acid, or a salt thereof, such as sodium alginate.

Dragee cores can be used in conjunction with suitable coatings, such as concentrated sugar solutions, which also can contain gum arabic, talc, polyvinylpyrrolidone, carbopol gel, polyethylene glycol, and/or titanium dioxide, lacquer solutions, and suitable organic solvents or solvent mixtures. Dyestuffs or pigments can be added to the tablets or dragee coatings for product identification or to characterize the quantity of active compound, i.e., dosage.

Pharmaceutical preparations that can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds can be dissolved or suspended in suitable liquids, such as fatty oils, liquid, or liquid polyethylene glycol with or without stabilizers.

Pharmaceutical formulations suitable for parenteral administration can be formulated in aqueous solutions, preferably in physiologically compatible buffers such as Hanks' solution, Ringer's solution, or physiologically buffered saline. Aqueous injection suspensions can contain substances that increase the viscosity of the suspension, such as sodium carboxymethyl cellulose, sorbitol, or dextran. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers also can be used for delivery. Optionally, the suspension also can contain suitable stabilizers or agents that increase the solubility of the compounds to allow for the preparation of highly concentrated solutions. For topical or nasal administration, penetrants appropriate to the particular barrier to be permeated are used in the formulation. Such penetrants are generally known in the art.

The pharmaceutical compositions of the present invention can be manufactured in a manner that is known in the art, e.g., by means of conventional mixing, dissolving, granulating, dragee-making, levigating, emulsifying, encapsulating, entrapping, or lyophilizing processes. The pharmaceutical composition can be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation can be a lyophilized powder which can contain any or all of the following: 1–50 mM histidine, 0.1%–2% sucrose, and 2–7% mannitol, at a pH range of 4.5 to 5.5, that is combined with buffer prior to use.

Further details on techniques for formulation and administration can be found in the latest edition of REMINGTON'S PHARMACEUTICAL SCIENCES (Maack Publishing Co., Easton, Pa.). After pharmaceutical compositions have been prepared, they can be placed in an appropriate container and labeled for treatment of an indicated condition. Such labeling would include amount, frequency, and method of administration.

The hepsin antagonists may be obtained commercially. For example, the hepsin blocking peptide (catalog no. 10024) can be obtained from Cayman Chemical Company (Ann Arbor, Mich., USA). Each vial contains 200 micrograms of lyophilized peptide consisting of human hepsin amino acids 241–260. The sequence listing of the human hepsin amino acids, including sequence no. 241–260, can be found in U.S. Pat. No. 6,423,543 (at columns 45 and 46), incorporated herein by reference. The peptide can be used in conjunction with Cayman's hepsin polyclonal antibody affinity purified (catalog no. 10022) to block protein-antibody complex formation during analysis for hepsin.

From the foregoing description, it should now be appreciated that a novel method for treating or preventing infarction comprising administering a hepsin antagonist with a dosage effective to suppress or inactivate hepsin's expression. While the invention has been described with reference to a specific embodiment, the description is illustrative of the invention and is not to be construed as limiting the invention. Various modifications and applications may occur to those who are skilled in the art, without departing from the true spirit and scope of the invention.

What is claimed is:

1. A method for treating infarction of a patient comprising administering hepsin blocking peptides with a dosage effective amount of said hepsin blocking peptides to inactivate hepsin activity within 12 hours of post-infarction, wherein said blocking peptides consist of human hepsin amino acids sequence no. 241–260.

2. The method according to claim 1, wherein the infarction is cerebral infarction.

3. The method according to claim 1, wherein the infarction is myocardial infarction.

4. The method according to claim 1, wherein the step of administering the hepsin blocking peptides comprises delivering the hepsin blocking peptides orally or delivering the hepsin blocking peptides through an apparatus to an infarcted site, wherein the apparatus is a probe, a catheter or a cannula.

5. A method for treating infarction of a patient comprising administering a dose of hepsin antagonist to an infarcted region or an infarct-risk region with a dosage effective amount to inactivate hepsin activity at about the infarcted or infarct-risk region within 12 hours of post-infarction, wherein said hepsin antagonist is a hepsin blocking peptides consisting of human hepsin amino acids sequence no. 241–260.

6. The method according to claim 5, wherein the infarction is cerebral infarction.

7. The method according to claim 5, wherein the infarction is myocardial infarction.

8. The method according to claim 5, wherein the step of administering the hepsin blocking peptides comprises delivering the hepsin blocking peptides orally or delivering the hepsin blocking peptides through an apparatus to the infarcted or infarct-risk site, wherein the apparatus is a probe, a catheter or a cannula.

* * * * *